US008353957B2

(12) United States Patent
Miller et al.

(10) Patent No.: US 8,353,957 B2
(45) Date of Patent: Jan. 15, 2013

(54) EXPANDABLE MEDICAL DEVICE AND METHOD (75) Inventors: Keith E. Miller, Germantown, TN (US); Cristian A. Capote, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 260 days.

(21) Appl. No.: 12/763,883

(22) Filed: Apr. 20, 2010

(65) Prior Publication Data
US 2011/0257688 A1 Oct. 20, 2011

(51) Int. Cl.
*A61F 2/44* (2006.01)
*A61B 17/88* (2006.01)

(52) U.S. Cl. ..................... 623/17.11; 606/279

(58) Field of Classification Search .......... 606/246–279; 623/17.11–17.16
See application file for complete search history.

(56) References Cited

U.S. PATENT DOCUMENTS

| 3,875,595 | A | | 4/1975 | Froning |
| 4,554,914 | A | | 11/1985 | Kapp et al. |
| 4,932,975 | A | | 6/1990 | Main et al. |
| 5,002,576 | A | | 3/1991 | Fuhrmann et al. |
| 5,123,926 | A | * | 6/1992 | Pisharodi ............... 623/17.13 |
| 5,236,460 | A | | 8/1993 | Barber |
| 5,290,312 | A | | 3/1994 | Kojimoto et al. |
| 5,336,223 | A | | 8/1994 | Rogers |
| 5,423,816 | A | * | 6/1995 | Lin ............................... 606/247 |
| 5,458,642 | A | * | 10/1995 | Beer et al. ............... 623/17.13 |
| 5,480,442 | A | | 1/1996 | Bertagnoli |
| 6,375,682 | B1 | | 4/2002 | Fleischmann et al. |
| 6,419,704 | B1 | * | 7/2002 | Ferree ...................... 623/17.12 |
| 7,837,688 | B2 | * | 11/2010 | Boyer et al. ............ 606/86 A |
| 2002/0147496 | A1 | | 10/2002 | Belef et al. |
| 2003/0083749 | A1 | | 5/2003 | Kuslich et al. |
| 2004/0133280 | A1 | | 7/2004 | Trieu |
| 2004/0199252 | A1 | | 10/2004 | Sears et al. |
| 2005/0113924 | A1 | | 5/2005 | Buttermann |
| 2005/0251260 | A1 | * | 11/2005 | Gerber et al. ........... 623/17.13 |
| 2006/0200239 | A1 | | 9/2006 | Rothman et al. |
| 2007/0093901 | A1 | | 4/2007 | Grotz et al. |
| 2007/0173934 | A1 | | 7/2007 | Dickinson et al. |
| 2007/0173940 | A1 | | 7/2007 | Hestad et al. |
| 2007/0203580 | A1 | * | 8/2007 | Yeh ........................... 623/17.13 |
| 2007/0260315 | A1 | | 11/2007 | Foley et al. |
| 2007/0270855 | A1 | * | 11/2007 | Partin ............................ 606/72 |

(Continued)

FOREIGN PATENT DOCUMENTS
DE 20017962 U1 8/2001
(Continued)

OTHER PUBLICATIONS

Michael P. Steinmetz, MD, et al. Management of Metastatic Tumors of the Spine: Strategies and Operative Indications, Neurosurg Focus 11(6), American Association of Neurological Surgeons, 2001.

(Continued)

*Primary Examiner* — Alvin Stewart
*Assistant Examiner* — Jacqueline Johanas (57) ABSTRACT

Embodiments of the invention include expandable, implantable devices and methods. Devices may be inserted with a longitudinal biasing force between anatomical structures to be stabilized and then expanded laterally or otherwise filled to provide secure fixation between or among the anatomical structures. In some embodiments, an implant replaces one or more vertebral bodies, or portions of vertebral bodies, of the spine.

9 Claims, 7 Drawing Sheets

U.S. PATENT DOCUMENTS

| | | |
|---|---|---|
| 2008/0021556 A1 | 1/2008 | Edie et al. |
| 2008/0058930 A1 | 3/2008 | Edie et al. |
| 2008/0058931 A1 | 3/2008 | White et al. |
| 2008/0147189 A1 | 6/2008 | Melkent |
| 2008/0161933 A1 | 7/2008 | Grotz et al. |
| 2008/0167726 A1 | 7/2008 | Melkent |
| 2008/0188895 A1 | 8/2008 | Cragg et al. |
| 2009/0270987 A1 | 10/2009 | Heinz et al. |

FOREIGN PATENT DOCUMENTS

| | | |
|---|---|---|
| DE | 202005009478 U1 | 6/2005 |
| EP | 1212992 B1 | 11/2001 |
| EP | 1290993 A1 | 7/2002 |
| WO | 0103614 A1 | 1/2001 |
| WO | 2008086274 A2 | 7/2008 |
| WO | 2008103466 A1 | 8/2008 |
| WO | 2008144175 A1 | 11/2008 |
| WO | 2008148210 A1 | 12/2008 |

OTHER PUBLICATIONS

Thomas J. Errico, MD, et al., A New Method of Thoracic and Lumbar Body Replacement for SPinal Tumors: Technical Note, Congress of Neurological Surgeons Dept. of Orthopedics and Neurosurgery, New York University, Feb. 24, 1992.

* cited by examiner

EXPANDABLE MEDICAL DEVICE AND METHOD

FIELD OF THE INVENTION

The present invention relates generally to the field of replacing portions of the human structural anatomy with medical implants, and more particularly relates to an expandable implant and method for replacing skeletal structures such as one or more vertebrae or portions of vertebrae.

BACKGROUND

Figure 1:
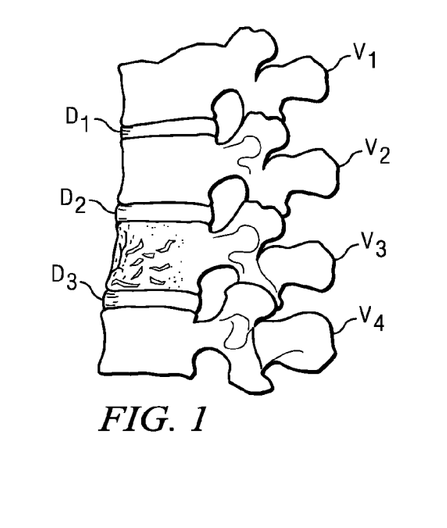
FIG. 1 is an elevation view of a segment of a lumbar spine.

It is sometimes necessary to remove one or more vertebrae, or a portion of the vertebrae, from the human spine in response to various pathologies. For example, one or more of the vertebrae may become damaged as a result of tumor growth, or may become damaged by a traumatic or other event. Removal, or excision, of a vertebra may be referred to as a vertebrectomy. Excision of a generally anterior portion, or vertebral body, of the vertebra may be referred to as a corpectomy. An implant is usually placed between the remaining vertebrae to provide structural support for the spine as a part of a corpectomy or vertebrectomy. FIG. 1 illustrates four vertebrae, $V_1$-$V_4$ of a typical lumbar spine and three spinal discs, $D_1$-$D_3$. As illustrated, $V_3$ is a damaged vertebra and all or a part of $V_3$ could be removed to help stabilize the spine. If removed along with spinal discs $D_2$ and $D_3$, an implant may be placed between vertebrae $V_2$ and $V_4$. In some cases, the implant inserted between the vertebrae is designed to facilitate fusion between remaining vertebrae. In other cases, especially when treating tumors, the ultimate goal of the procedure is spinal stability, regardless of fusion. A successful procedure may decrease pain, preserve or enhance neurological function and allow a patient greater mobility without an external orthosis. Sometimes an implant is designed to replace the function of the excised vertebra and discs. All or part of more than one vertebra may be damaged and require removal and replacement in some circumstances. If only a portion of a vertebral body and adjacent discs are removed and replaced, the procedure may be called a hemi-vertebrectomy.

Figure 2:
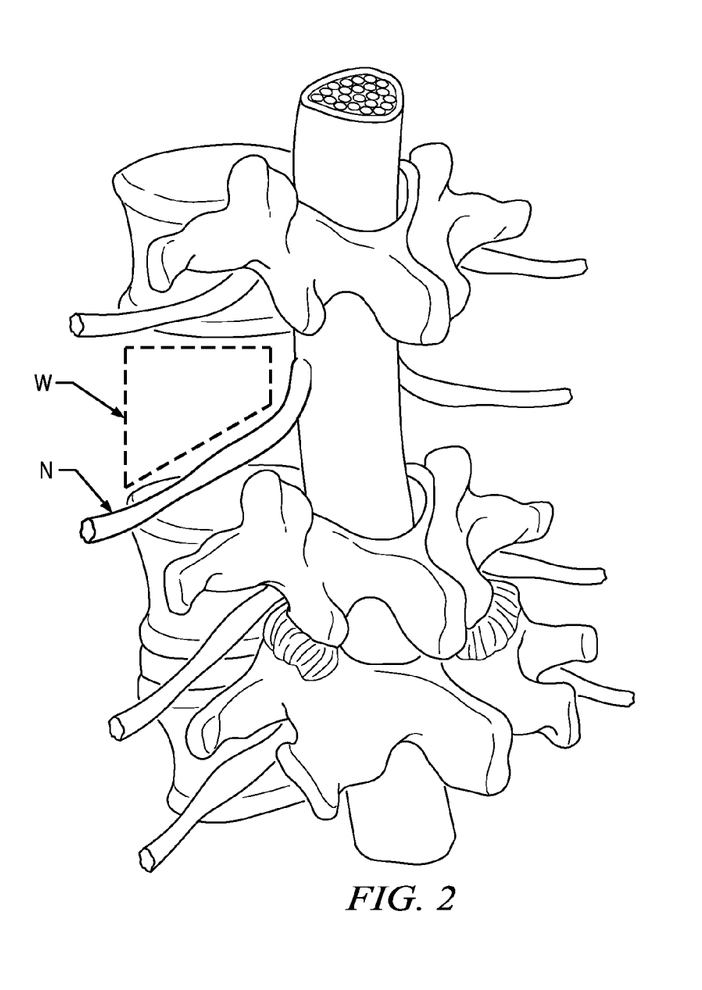
FIG. 2 is a posterior perspective view of a portion of a human spine.

Many implants are known in the art for use in vertebrectomy and corpectomy procedures. One class of implants is sized to directly replace the vertebra or vertebrae that are being replaced, without in situ expansion. Another class of implants is inserted in a collapsed state and then expanded once properly positioned. Expandable implants may be advantageous because they allow for a smaller incision and entry path when positioning an implant. A smaller incision may be particularly useful with a posterior approach, as illustrated in FIG. 2. FIG. 2 is an illustration from the posterior of a portion of a human spine, with one vertebra removed. To support the remaining vertebral structure, an implant may be placed through the window W, avoiding the nerve root N. The nerve root N, may be mobilized to increase the size of the window W slightly, but excess movement may risk damage to the nerve root N. Therefore, for a posterior approach, an initially small expandable implant may have particular utility. A posterior approach may be preferred for patients with circumferential tumors or for patients more susceptible to the risks associated with a more extensive anterior approach. Similarly, initially small implants enabling minimal tissue disruption may be useful from any surgical approach to reduce trauma to surrounding tissues and to enhance patient recovery.

Once in position and expanded, it may be advantageous for a corpectomy or vertebrectomy implant to, as nearly as possible, fill the space vertically between the remaining vertebrae and laterally among the remaining soft tissues. Lateral expansion may increase the contact area between the implant and vertebral endplates. This expansion may reduce the potential for subsidence of the device into the adjacent vertebrae. It may be advantageous in some embodiments to provide an implant that will exert a biasing force against remaining vertebrae prior to filling with a material to otherwise expand the implant. It may be advantageous in some embodiments to provide an implant that may be provisionally positioned and held at a surgical site from a grasping point.

Expandable implants may also be useful in replacing long bones or portions of appendages such as the legs and arms, or a rib or other bone that is generally, though not necessarily, longer than it is wide. Examples include, but are not limited to a femur, tibia, fibula, humerus, radius, ulna, phalanges, clavicle, and any of the ribs. Use of the mechanisms described and claimed herein are equally applicable to treatment or repair of such bones or appendages. Similarly, expandable implants may be useful in at least some spinal fusion procedures where a spinal disc is replaced without replacing a vertebral body.

SUMMARY

One embodiment of the invention is a method of stabilizing spaced apart skeletal structures. The method may include providing an expandable medical implant with a membrane defining a volume and including an upper surface, a substantially opposite lower surface and a lateral diameter, and a biasing member including a first end, a substantially opposite second end, and a lateral diameter, wherein the biasing member is coupled to the membrane. The method may also include grasping the first end of the biasing member, placing the second end of the biasing member against a second skeletal structure to compress the biasing member, and aligning the first end of the biasing member with a first skeletal structure. Embodiments of the method may include releasing compression of the biasing member to allow the expandable medical implant to contact the first skeletal structure, and introducing fill material into the expandable medical implant to one or both maintain expansion and cause expansion of the expandable medical implant.

Another embodiment of the invention is a method of stabilizing a portion of a vertebral column. The method may include removing at least a portion of one or more vertebrae from a space between a first vertebra and a second vertebra, inserting a medical implant having a length into the space between the first vertebra and the second vertebra, and forcing the medical implant against the second vertebra to decrease the length of the medical implant. The method may also include allowing the medical implant to expand in length to come into contact with the first vertebra, and introducing a fill material into the medical implant to expand the medical implant laterally to occupy a portion of the space between the first vertebra and the second vertebra.

Yet another embodiment of the invention is an expandable medical implant for supporting skeletal structures that are spaced apart along a longitudinal axis. The expandable medical implant may have a membrane defining a volume and including an upper surface, a substantially opposite lower surface, a side between the upper and lower surfaces, and a lateral diameter substantially transverse to the longitudinal axis. The expandable medical implant may also have a biasing member coupled to the membrane and include a first end, a substantially opposite second end, and a lateral diameter substantially transverse to the longitudinal axis. The biasing member in an expanded state may be longer than the distance between the spaced apart skeletal structures to be supported. The lateral diameter of the membrane when at least partially filled in some embodiments is larger than the lateral diameter of the biasing member.

DETAILED DESCRIPTION

The following documents are incorporated by reference herein in their respective entireties: U.S. patent application Ser. No. 12/424,663, entitled, "VERTEBRAL ENDPLATE CONNECTION IMPLANT AND METHOD;" U.S. patent application Ser. No. 12/424,941, entitled, "MINIMALLY INVASIVE EXPANDABLE VERTEBRAL IMPLANT AND METHOD;" U.S. patent application Ser. No. 12/424,880, entitled, "MINIMALLY INVASIVE EXPANDABLE CONTAINED VERTEBRAL IMPLANT AND METHOD;" and U.S. patent application Ser. No. 12/424,666, entitled, "DEPLOYMENT SYSTEM AND METHOD FOR AN EXPANDABLE VERTEBRAL IMPLANT;" each application filed on Apr. 16, 2009.

An embodiment of an expandable medical implant 1 is illustrated in FIGS. 3-6C. The expandable medical implant 1 is shown supporting skeletal structures that are spaced apart along a longitudinal axis L. The skeletal structures depicted are a first vertebra V1 and a second vertebra V2. The first vertebra V1 and the second vertebra V2 are separate bones, but in other embodiments, an expandable medical implant, as disclosed herein, may be deployed to support parts of a single bone or skeletal structure that has been at least partially fractured or otherwise altered.

Figure 3:
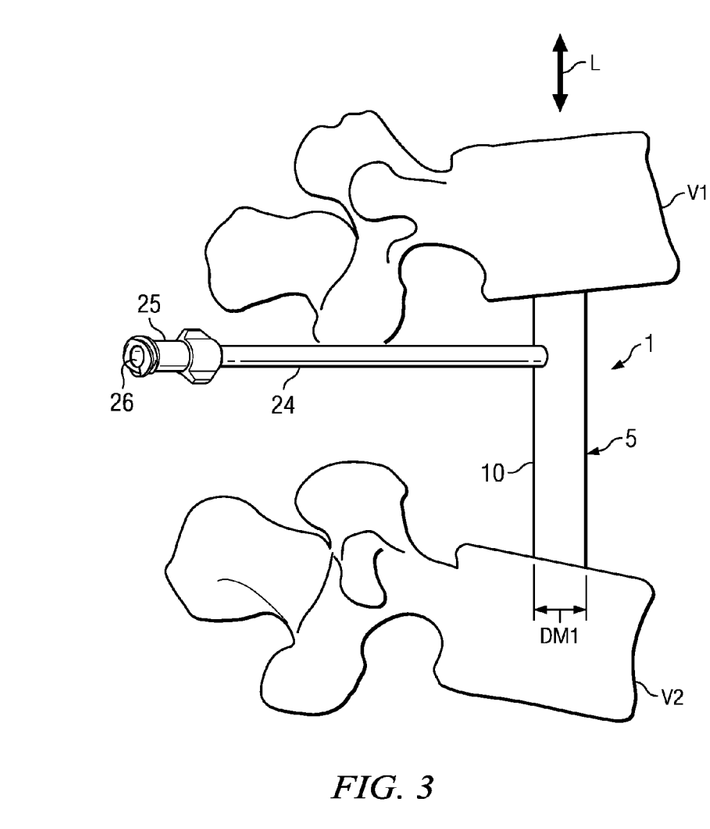
FIG. 3 is a side elevation view of an embodiment of an expandable medical implant in a laterally unexpanded state between vertebrae.
Figure 4:
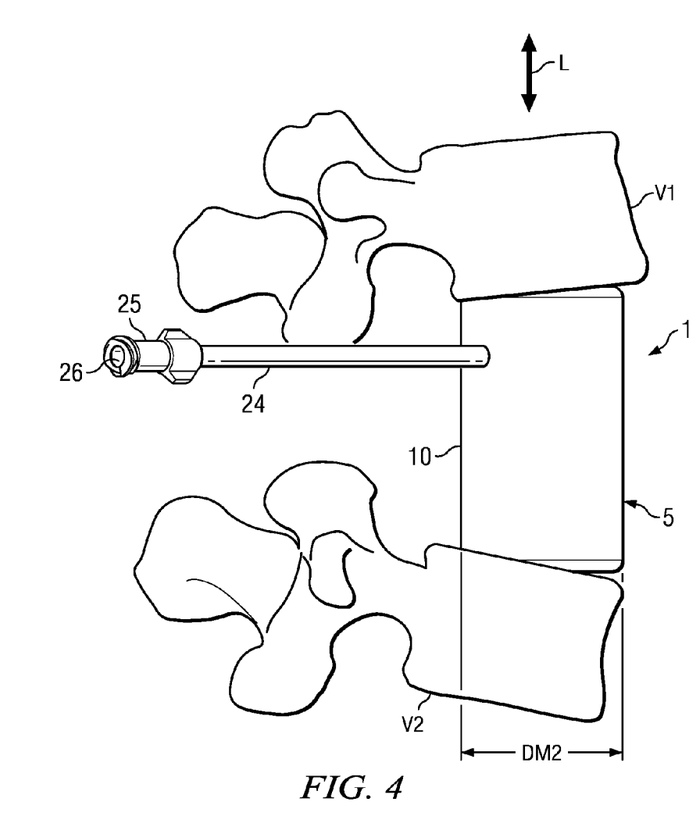
FIG. 4 is a side elevation view of the embodiment of FIG. 3 in an at least partially laterally expanded state.
Figure 5A:
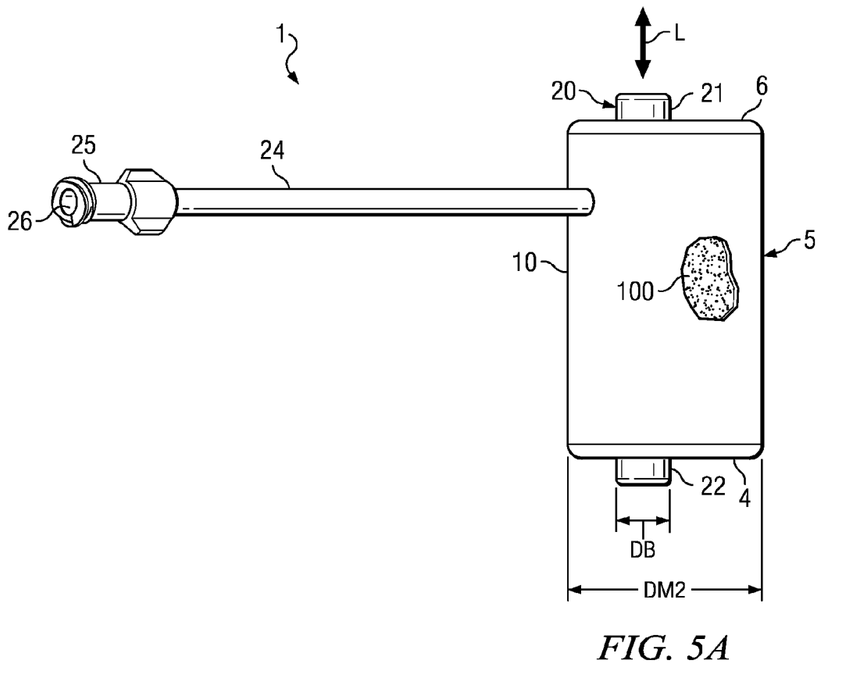
FIG. 5A is a side elevation view of the embodiment of FIG. 3 with a partial cut-away and in an at least a partially laterally expanded state.
Figure 5B:
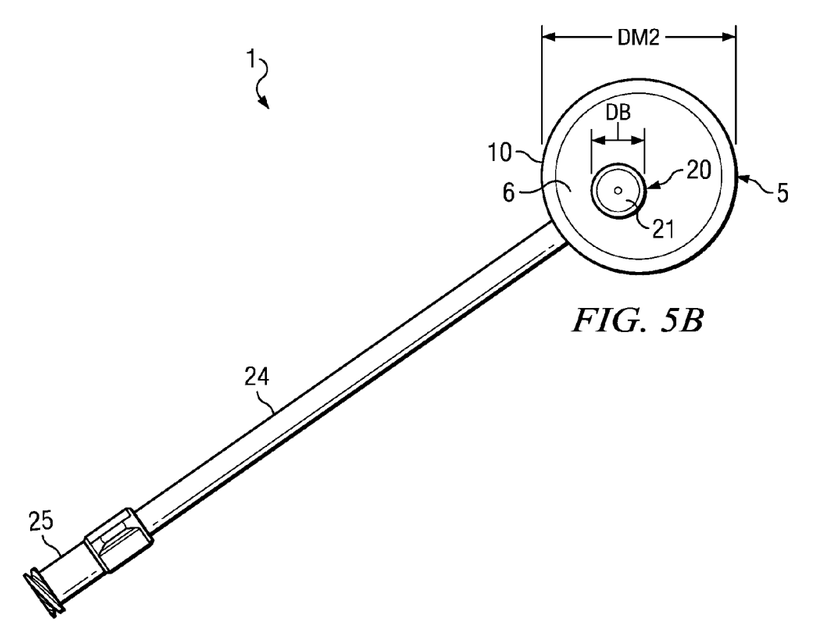
FIG. 5B is a top plan view of the embodiment of FIG. 5A.

The expandable medical implant 1 illustrated in FIGS. 3-5B includes a membrane 5 defining a volume and having an upper surface 6 (FIGS. 5A and 5B), a substantially opposite lower surface 4 (FIG. 5A), a side 10 between the upper and lower surfaces 6, 4, and a lateral diameter substantially transverse to the longitudinal axis L. A first lateral diameter DM1 of the membrane 5 is shown in FIG. 3 where the expandable medical implant 1 is depicted in an unfilled state, or state prior to lateral expansion. As used herein with regard to embodiments of expandable medical implants, the term "lateral" means directions substantially transverse to the illustrated longitudinal axis L. A second lateral diameter DM2 of the membrane 5 is shown in FIGS. 4-5B where the expandable medical implant 1 is depicted in an at least partially filled state, or state following at least partial lateral expansion. The term "diameter" as used herein refers to any maximal breadth that is substantially transverse to a longitudinal axis, such as the longitudinal axis L. A "diameter" is not necessarily associated with a circular or elliptical shape. As shown in FIGS. 3-5B, the cross-sectional shape of the embodiment of the membrane 5 is generally round. However, in other embodiments, the cross-sectional shape of the membrane 5 may be any functional shape, such as but not limited to, concave-convex, oval, rectangular, triangular, polygonal, or combinations of these shapes.

The membrane 5 of some embodiments is configured to be placed between first and second vertebrae V1, V2 such that the upper surface 6 contacts the first vertebra V1, and the opposite lower surface 4 contacts the second vertebra V2 to provide support between the first and second vertebrae V1, V2. Lateral expansion of the membrane 5 is also accomplished in some embodiments. For example, in FIGS. 4-5B, anterior, posterior, and medial-lateral expansion, and intervening radial expansions, are illustrated.

The membrane 5 may be constructed, in whole or in part, of a non-permeable material. The membrane 5 may include compliant or non-compliant balloon materials such as those commonly used to manufacture coronary and Kyphoplasty medical devices. Such materials may include, but are not limited to, mylar, rubber, polyurethane, vinyl, latex, polyethylenes, ionomer, and polyethylene terephthalate (PET), as well as less flexible materials such as Kevlar®, PEBAX®, stainless steel, titanium, nickel-titanium alloys, and other metals and alloys and/or ceramics. A compliant membrane may include reinforcing to limit one or both of the size and shape of the membrane to a clinically advantageous extent. A non-compliant membrane may expand more elastically to more completely fill an irregular opening, depending on the amount of material introduced into the membrane.

The membrane 5 may be constructed, in whole or in part, of a permeable material, which allows a certain amount of a fill material to pass through the membrane 5. All or a portion of the membrane 5 may be made permeable by fabricating a material, including but not limited to, the membrane materials listed above, into a fabric, weave, mesh, composite, bonded fiber assembly, or any other manufacture known to those skilled in the art. For example, all or part of the upper surface 6 and the opposite lower surface 4 may be constructed of a permeable material to allow a fill material to move through the membrane 5 and to come into contact with vertebrae.

A biasing member 20 coupled to the membrane 5 is illustrated in a combination of views in FIGS. 5A-6C. The biasing member 20 shown includes a first end 21, a substantially opposite second end 22, and has a lateral diameter DB substantially transverse to the longitudinal axis L. A spring 23 is shown coupled between the first end 21 and the second end 22. In some embodiments, the biasing member 20 is longer than the distance between spaced apart skeletal structures to be supported when the biasing member is in an expanded state. The surfaces of the spaced apart skeletal structures to which the biasing member 20 couples are irregular in many circumstances. Therefore, the distance between the spaced apart skeletal structures as used herein means a distance from a contact point of the biasing member 20 on one skeletal structure to a contact point of the biasing member 20 on the other skeletal structure, as the respective contact points are spaced in a finally secured skeletal structure.

Figure 6A:
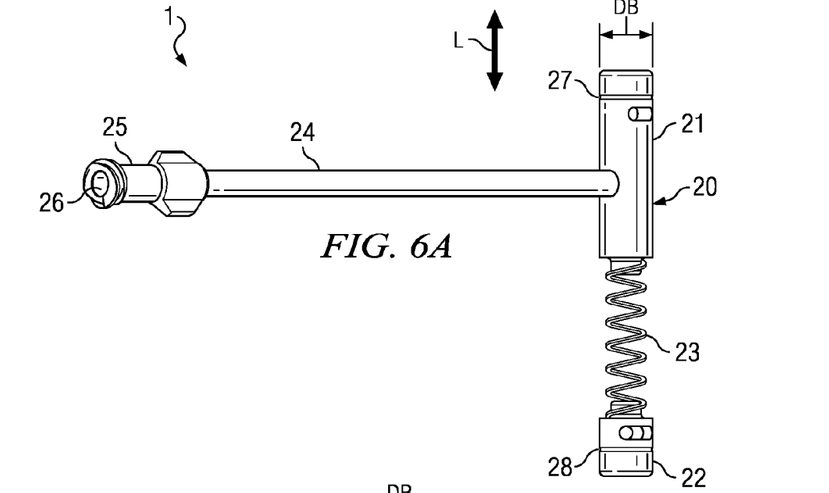
FIG. 6A is a side elevation view of a portion of the embodiment of FIG. 3.
Figures 6B, 6C:
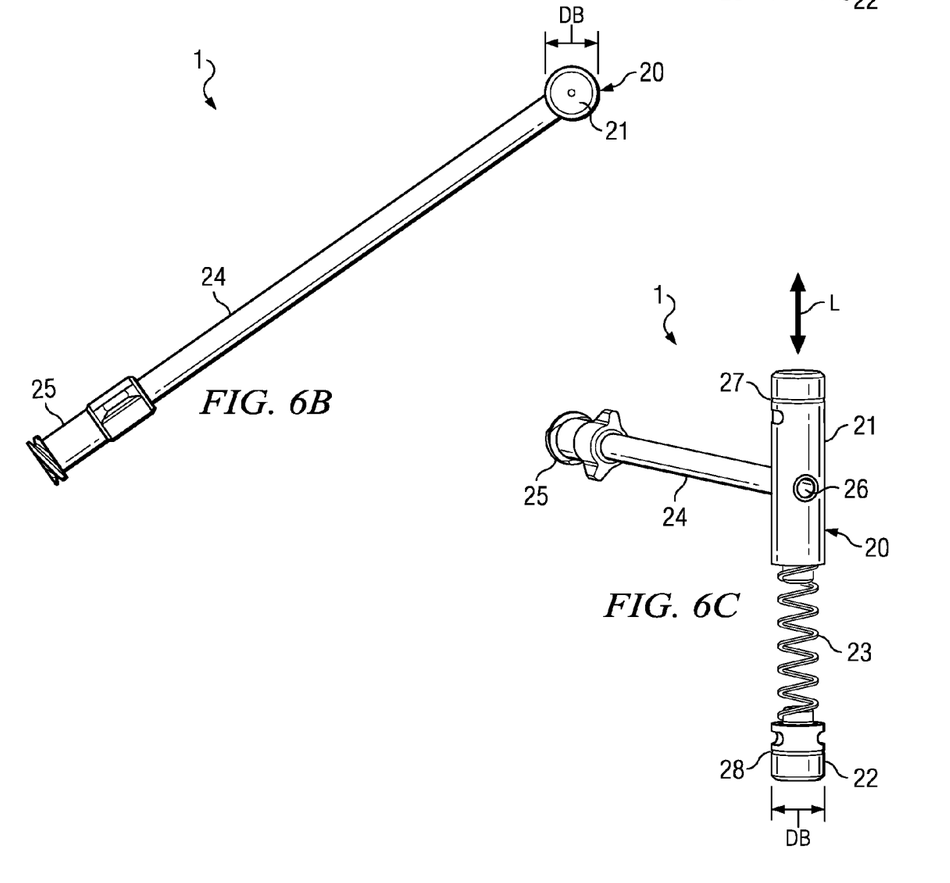
FIG. 6B is a top plan view of the embodiment of FIG. 6A.
FIG. 6C is an alternative side elevation view of the embodiment of FIG. 6A.

An example length of the biasing member 20 in an expanded state is shown in FIGS. 5A, 6A, and 6C by the overall vertical dimension of the biasing members 20 depicted there. This length may be reduced in the example by compressing the spring 23 shown in FIGS. 6A and 6C. The spring 23 may be compressed by pressing together the first end 21 and the second end 22. A distance between spaced apart skeletal structures is illustrated in FIGS. 3 and 4. By providing a biasing member 20 that is longer than the distance between spaced apart skeletal structures, forces are exerted against the spaced apart skeletal structures by the biasing member 20 when the biasing member 20 is placed between the skeletal structures and released. These forces may be useful to provisionally hold the biasing member 20 between the skeletal structures while other tasks such as alignment or filling of the expandable medical implant 1 are being performed or for any other effective purpose. The fact that the biasing member 20 is of a variable length may also make insertion of the expandable medical implant 1 into position between skeletal structures easier, as will be discussed in greater detail in association with method embodiments herein. The amounts of the forces exerted against the spaced apart skeletal structures and the travel distance can be altered by altering the length and stiffness of the spring 23. In addition to a helical spring, as is illustrated, any other effective type of spring or biasing element may be used. For example and without limitation, a biasing member may have a spring force generated by a leaf spring, a wave element, randomly arranged spring elements, an elastomer, a pneumatic force generator, or a magnetic force generator.

As shown in FIG. 5A, the biasing member 20 is coupled to the membrane 5 near the first end 21 of the biasing member 20 near the upper surface 6 of the membrane 5. The illustrated biasing member 20 is also coupled to the membrane 5 near the second end 22 of the biasing member 20 near the lower surface 4 of the membrane 5. At either or both of the first and second ends 21, 22, the biasing member 20 may fit through a grommet or reinforced section of the membrane 5 and form a seal between the biasing member 20 and the membrane 5. Any effective type of adhesive or welding may be used to couple the biasing member 20 and the membrane 5. Additionally, or alternatively, a clamp or spring of any effective type may be used to fasten the biasing member 20 and the membrane 5. For example and without limitation, one or more spring clips (not shown) may be placed over the membrane 5 near either or both of the upper surface 6 and the lower surface 4 and into a first groove 27 and a second groove 28 to couple the membrane 5 to the biasing member 20. Also, grommets or reinforced sections may be configured to seat in one or both of the first groove 27 and the second groove 28.

In the embodiment illustrated in FIGS. 5A and 5B, the biasing member 20 is substantially contained within the volume of the membrane 5. Although the first and second ends 21, 22 protrude from the membrane 5, as used herein, the biasing member 20 is considered substantially contained within the membrane 5. In other embodiments, the biasing member may be completely retained within the membrane 5. In still other embodiments, all or a majority of the biasing member 20 may be outside of the volume of the membrane 5. Examples of members with all or a majority of a member outside of the volume of the membrane 5 may be found in U.S. patent application Ser. No. 12/424,941, entitled, "MINIMALLY INVASIVE EXPANDABLE VERTEBRAL IMPLANT AND METHOD," which is incorporated by reference herein above. Example embodiments include the laterally rigid component of the '941 application replaced by a biasing member and similarly used in combination with a membrane, and any other effective combinations.

In some embodiments, the membrane 5 may be coupled to the biasing member 20 along a side, such as the side 10, of the membrane 5 to restrict lateral expansion of the membrane in at least a first direction. Resistance to lateral forces may be useful in various embodiments for protecting posterior or other neural or vascular structures such as, but not limited to, the spinal cord, spinal canal, and nerve roots. Embodiments directed to coupling along a side of a membrane and laterally rigid devices are described in greater detail in association with U.S. patent application Ser. No. 12/424,880, entitled, "MINIMALLY INVASIVE EXPANDABLE CONTAINED VERTEBRAL IMPLANT AND METHOD," and are incorporated by reference as noted herein above. Example embodiments include the laterally rigid component of the '880 application replaced by a biasing member and similarly used in combination with a membrane, and any other effective combinations.

As illustrated in FIGS. 3-6C, the expandable medical implant 1 includes an extension 24 coupled to the first end 21 of the biasing member 20. The extension 24 may be used to manipulate the expandable medical implant 1. The extension 24 is made from at least one relatively stiff material in some embodiments. The extension 24 shown includes a port 26 (FIGS. 3, 4, 5A, 6A, and 6C) through the extension 24 through which a fill material may be introduced into the expandable medical implant 1. As shown in FIG. 6C, the port 26 passes through a portion of the first end 21 of the biasing member 20 and communicates with the volume inside the membrane 5. The membrane 5 may include a seal configured to move along the extension 24 as the membrane 5 is filled. In some embodiments, the membrane 5 includes or is attached to a sleeve that extends along a length of the extension 24 such that the sleeve is rolled away from the biasing member 20, but maintains a seal along the extension 24, as the membrane 5 is filled. In the illustrated embodiment, the extension 24 includes a luer lock connection component 25 for securely connecting the expandable medical implant 1 to a fill material source. Any other effective fluid connection device or method may be used to connect a fill material source to the expandable medical implant 1. In other embodiments, a port for fill material may be provided at any effective location on the expandable medical implant 1, including but not limited to, directly into a membrane or into either or both of first and second ends of a biasing member or similar components.

Figure 7A:
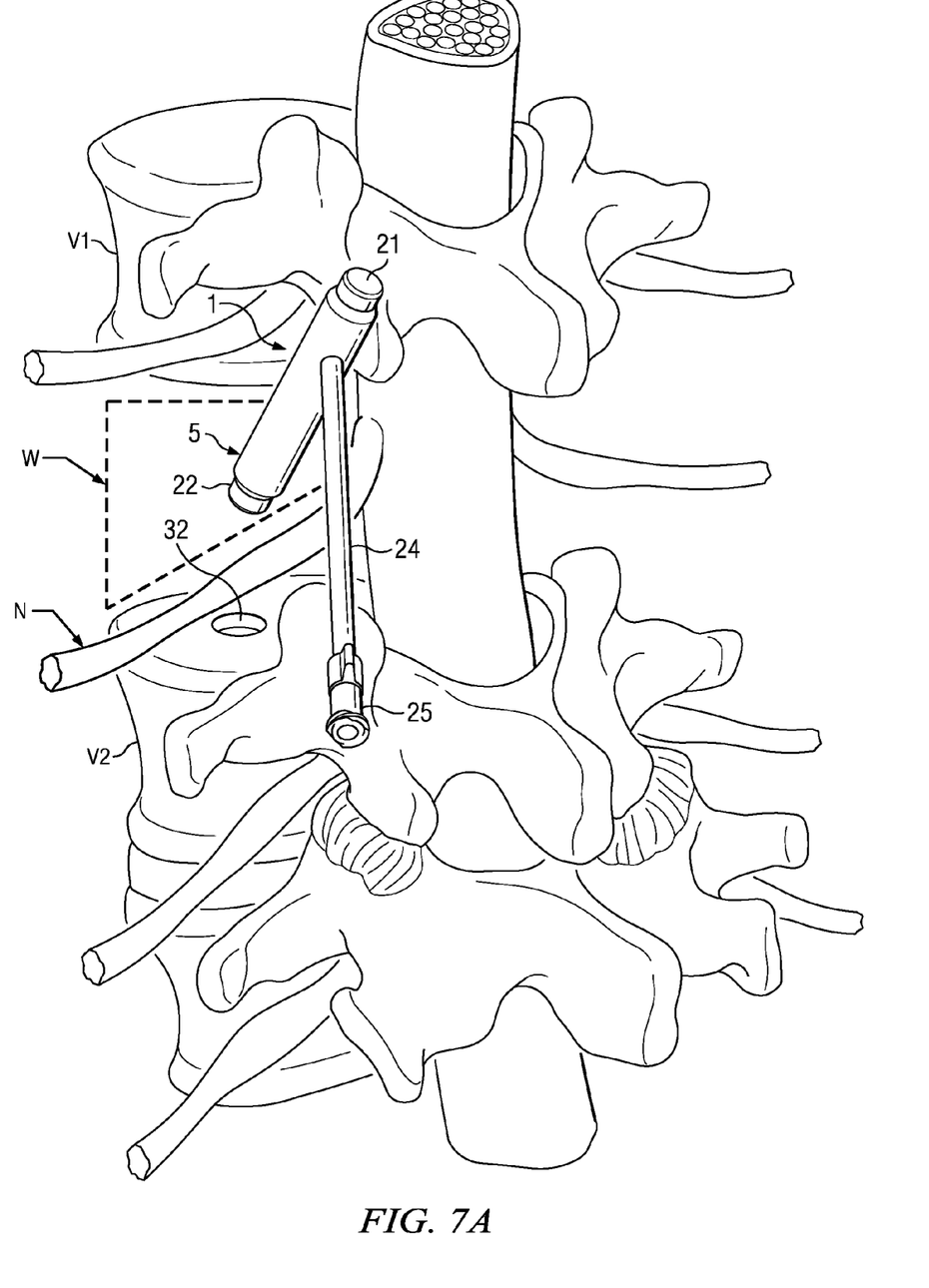
FIG. 7A is a posterior perspective view of an expandable medical implant being applied to a portion of a human spine.
Figure 7B:
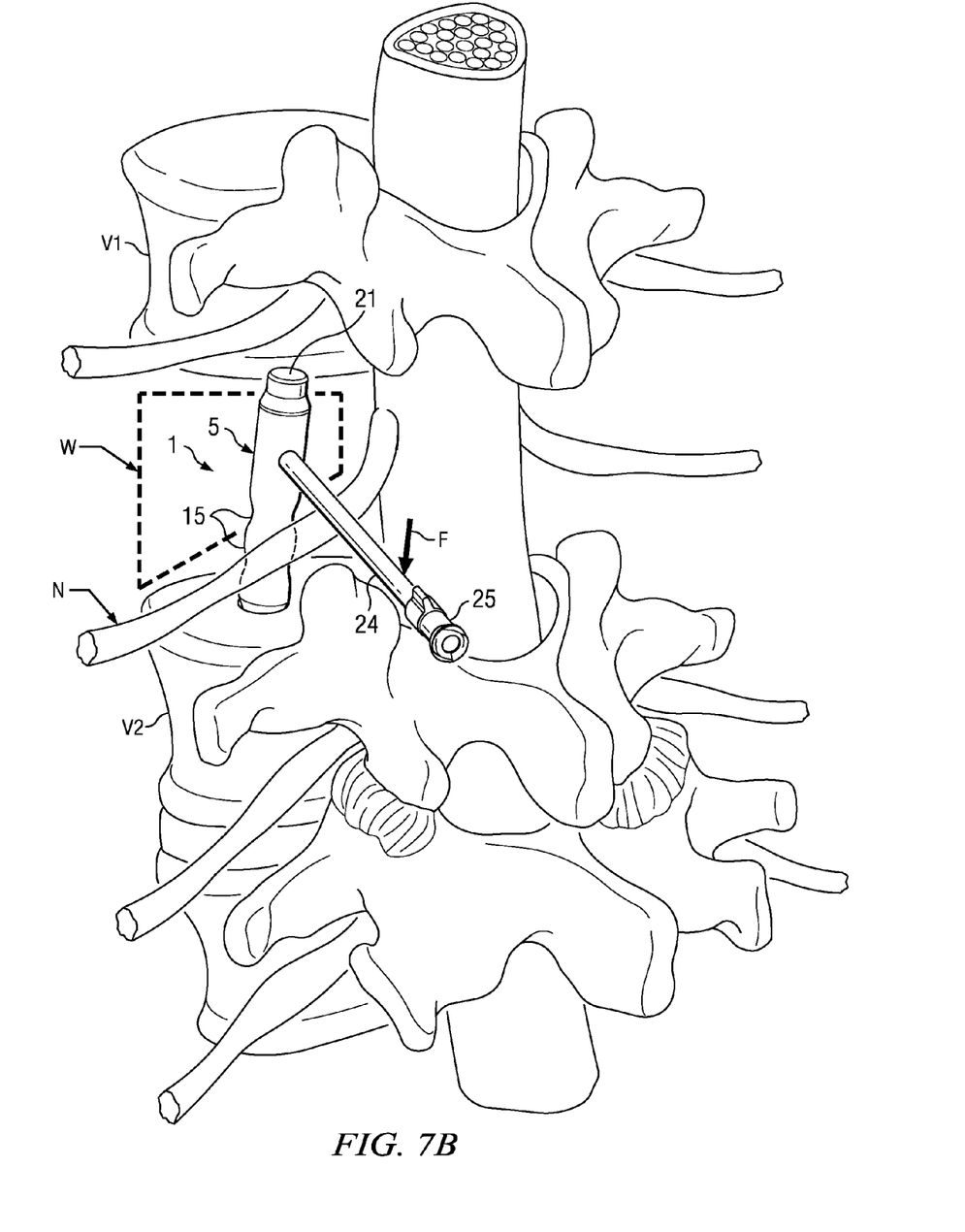
FIG. 7B is a posterior perspective view of an expandable medical implant being applied to a portion of a human spine.

In some embodiments, the expandable medical implant may include a protrusion configured to enter a cavity formed in one or more skeletal structures. For example, in the illustrated embodiments, the outward extents of the first end 21 or the second end 22 of the biasing member may serve as a protrusion configured to enter a cavity formed in one or more skeletal structures. A protrusion may further serve as a nozzle through which fill material may be passed into the one or more skeletal structures. A cavity 32 in a second vertebra V2 is illustrated in FIG. 7A, and a second end 22 of the biasing element 20 is shown in FIG. 7B having been entered into the cavity 32. A similar cavity may be provided in the endplate of a first vertebra V1. Multiple devices for forming an opening or cavity and multiple protrusion or nozzle embodiments are disclosed in U.S. patent application Ser. No. 12/424,663, entitled, "VERTEBRAL ENDPLATE CONNECTION IMPLANT AND METHOD," all of which are incorporated by reference as noted herein above. These and other structures to effectively engage skeletal structures are contemplated. In some embodiments, portions of the membrane 5 may extend over outward extents of one or both of the first end 21 and the second end 22 serving as nozzles and be held in this position against skeletal structures by spring forces of the biasing member 20. As fill material is introduced into the membrane 5, the portions of the membrane 5 extending over outward extents of the first end 21 and the second end 22 may be pulled back from the ends 21, 22 to allow fill material to pass through nozzles and into skeletal structures as discussed herein. These embodiments may be useful to govern the sequence of fill material flow in operation of embodiments of the invention.

A fill material may be introduced into the expandable medical implant 1 as a fluid, and then harden or cure in the implant. In some embodiments, a non-hardenable and non-curing fluid may be used to fill the implant or one or some of the components of the implant. A fill material 100, as illustrated in FIG. 5A may be introduced into at least the membrane 5 to provide support between the upper surface 6 and the lower surface 4. The fill material 100 may be a paste, gel, liquid, suspension, granular mixture, or similar substance. Non-limiting examples of fill materials 100 include bone cement, paste, morselized allograft, autograft, or xenograft bone, ceramics, or various polymers. An example bone cement is polymethylmethacrylate (PMMA), which may be made from methylmethacrylate, polymethylmethacrylate, esters of methacrylic acid, or copolymers containing polymethylmethacrylate and polystyrene. Additional non-limiting examples of the fill material 100 include semi-rigid flowable or hardenable material such as silicone or various types of urethane materials. It should further be understood that other types of fill materials 100 which are not necessarily hardenable or curable may be used in association with the present invention. For example, the fill material 100 may comprise beads or small particles or grains of material, some of which may, in aggregate, achieve a harder consistency as a result of interlocking or compaction. In some embodiments, the fill material 100 may also include any bone growth promoting substance.

Where the fill material 100 is a hardenable material, the biasing member 20 may serve as a reinforcing element within the hardened fill material 100. For example and without limitation, a steel or titanium alloy biasing member encapsulated within a PMMA fill material would provide additional reinforcement to the PMMA when hardened and bonded to and encapsulating the biasing member. Placement of the biasing member reinforcement alone or in combination with other reinforcement may be arranged to give the expandable medical implant particular strength and deflection characteristics.

Embodiments disclosed herein may be described as a means for occupying a vertebral space. The means for occupying a vertebral space may include a containment means defining a volume, and a linearly biased means coupled to the containment means. The linearly biased means may be substantially located within the volume of the containment means in some embodiments, or may be have a majority of the biasing means outside of the containment means in other embodiments. In some embodiments, the containment means is a membrane that is placed into the vertebral space in an unexpanded state and is then expanded laterally to occupy a desired portion of the vertebral space. The linearly biased means when in an expanded state may be of a greater length than the space into which it is placed. The linearly biased means may also linearly expand the containment means in some embodiments. The containment means may be configured to occupy a vertebral space to the extent of soft tissues that surround the spinal column. These soft tissues may include, but are not limited to, one or more of ligaments, muscles, vessels, arteries, and neural structures.

For embodiments of each of the implants disclosed herein, the size or shape of the membrane may be limited to only fill a particular portion of a vertebral space. For example, and without limitation, an implant may be configured to only occupy a lateral portion of a vertebral space to accomplish a hemi-vertebrectomy. Implants may be alternatively shaped to occupy other, limited portions of a vertebral space.

Embodiments of the implant in whole or in part may be constructed of biocompatible materials of various types. Examples of implant materials include, but are not limited to, non-reinforced polymers, carbon-reinforced polymer composites, PEEK and PEEK composites, low density polyethylene, shape-memory alloys, titanium, titanium alloys, cobalt chrome alloys, stainless steel, ceramics and combinations thereof. If a trial instrument or implant is made from radiolucent material, radiographic markers can be located on the trial instrument or implant to provide the ability to monitor and determine radiographically or fluoroscopically the location of the body in the spinal space. In some embodiments, the implant or individual components of the implant may be constructed of solid sections of bone or other tissues. Tissue materials include, but are not limited to, synthetic or natural autograft, allograft or xenograft, and may be resorbable or non-resorbable in nature. Examples of other tissue materials include, but are not limited to, hard tissues, connective tissues, demineralized bone matrix and combinations thereof.

Some embodiments of the invention may be applied in the lumbar spinal region. Some embodiments may be applied to the cervical or thoracic spine or between other skeletal structures.

Some embodiments may also include supplemental fixation devices in addition to or as part of the expandable medical implant for further stabilizing the anatomy. For example, and without limitation, rod and screw fixation systems, anterior, posterior, or lateral plating systems, facet stabilization systems, spinal process stabilization systems, and any devices that supplement stabilization may be used as a part of or in combination with the expandable medical implant. Embodiments of the invention may be useful in at least some spinal fusion procedures where a spinal disc is replaced without replacing a vertebral body.

Figure 7C:
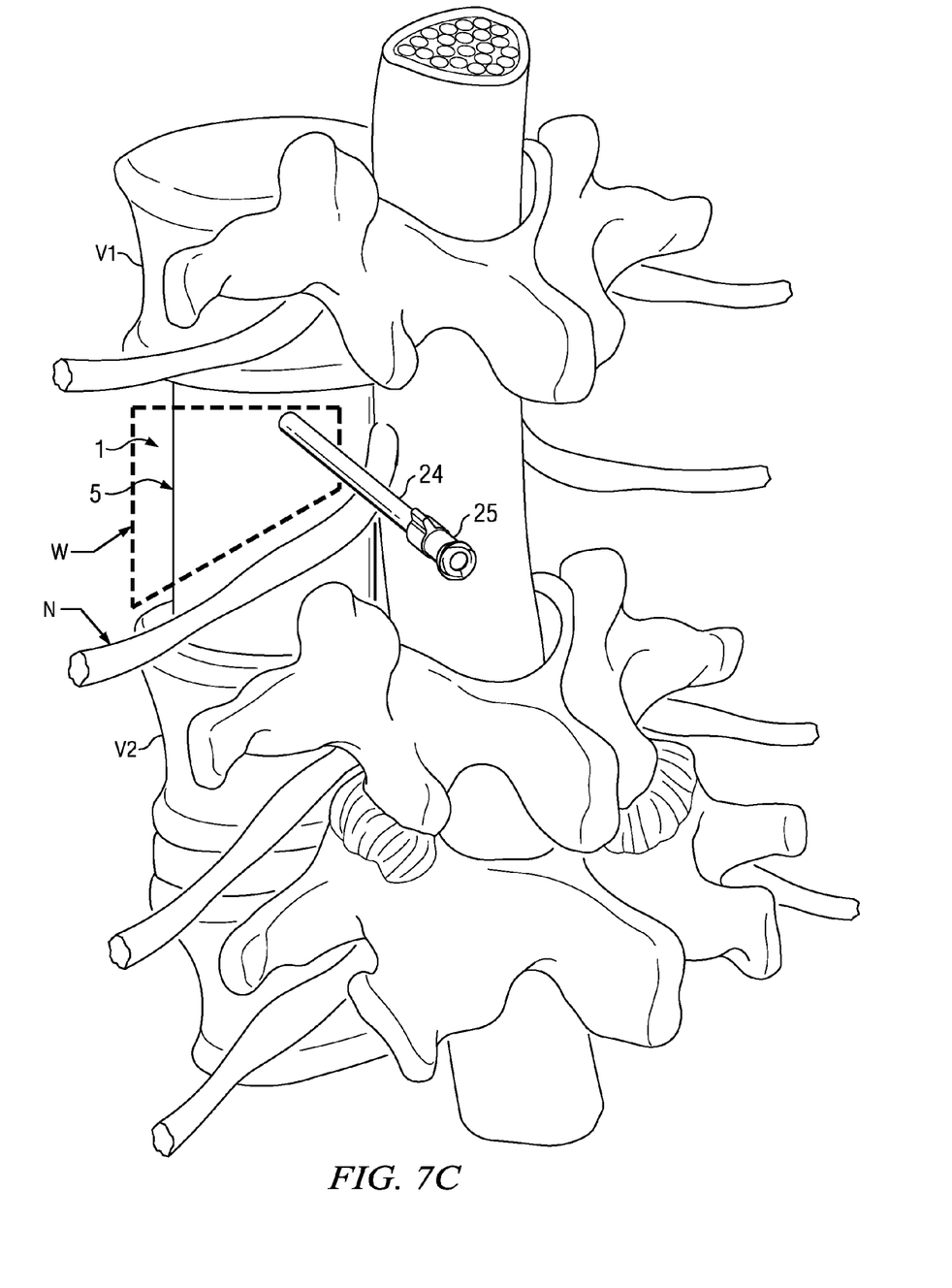
FIG. 7C is a posterior perspective view of an expandable medical implant being applied to a portion of a human spine.

An embodiment of the invention is a method of stabilizing spaced apart skeletal structures, such as but not limited to, the first vertebra V1 and the second vertebra V2, as illustrated in FIGS. 7A-7C. The expandable medical implant 1, as described in greater detail herein, may be provided in the disclosed method. Other expandable medical implants may be used in various embodiments of the methods disclosed. The example expandable medical implant 1 includes a membrane 5 defining a volume and including an upper surface 6, a substantially opposite lower surface 4, and a lateral diameter DM1, DM2 (FIGS. 3 and 5A). A biasing member 20 including a first end 21, a substantially opposite second end 22, and a lateral diameter DM, as illustrated in FIG. 6A, may also be provided. The illustrated biasing member 20 is coupled to the membrane 5.

Method embodiments may include grasping the first end 21 of the biasing member 20. The first end 21, or one or more members coupled to the first end 21, may be grasped directly by a user, with a clamp, pliers, other tool, or a specialized instrument or component that interfaces with the first end 21 in any effective manner. In the example illustrated, the first end 21 is grasped by interconnection with the extension 24 and subsequent control of the extension 24. Control or grasping of the extension 24 may likewise be accomplished in any effective manner.

Method embodiments may also include placing the second end 22 of the biasing member 20 against a second skeletal structure, such as the second vertebra V2 to compress the biasing member 20. The second end 22 of the biasing member 20 is shown in FIG. 7A being inserted through the window W past the nerve root N. The window W is created among the soft tissues of a segment of the spinal column. The second end 22 of the expandable medical implant 1 was introduced through the window W first, in the illustrated embodiment. In other embodiments, another portion of an expandable medical implant may be introduced first and other translational and rotational manipulations may be conducted as the implant is introduced. FIG. 7B further illustrates the second end 22 against the second vertebra V2 and the application of a force F to compress the biasing member 20. The force F is a pushing linear force to compress the biasing member 20, but in other embodiments the force may be a pulling, twisting, combination force, or any effective force to compress a complementary biasing member. Deformations 15 in the membrane 5 are illustrated in FIG. 7B, indicating compression in the underlying spring 23 of the biasing member 20 and buckling of the membrane 5. The biasing member 20 may be further compressed to cause the first end 21 to clear the first vertebra V1. The first end 21 of the biasing member 20 may then be aligned with the first vertebra V1, as illustrated in FIG. 7C. This alignment may be carried out under direct vision, with the aid of optical instruments, in combination with radiographic equipment or surgical navigation equipment, or by any other effective mechanism. The method illustrated in FIGS. 7A-7C illustrates that a cavity 32 has been formed in the second vertebra V2. Multiple devices and methods for forming an opening or cavity are disclosed in U.S. patent application Ser. No. 12/424,663, entitled, "VERTEBRAL ENDPLATE CONNECTION IMPLANT AND METHOD," which is incorporated by reference as noted herein above. In the illustrated embodiment, the act of placing the second end 22 of the biasing member 20 against the second skeletal structure includes placing the second end 22 of the biasing element 20 into the cavity 32.

Method embodiments may also include releasing compression of the biasing member 20 to allow the expandable medical implant 1 to contact the first skeletal structure, as illustrated in FIG. 7C. The biasing member 20 of the illustrated embodiment has been release to allow contact with the first vertebra V1. A cavity similar to the cavity 32 provided in the endplate of the second vertebra V2 may be provided in the endplate of a first vertebra V1 in some embodiments.

As also illustrated in FIG. 7C, fill material may be introduced into the expandable medical implant to maintain expansion or cause expansion of the expandable medical implant 1. In some embodiments, the fill material is the fill material 100 disclosed herein. The membrane 5 of the expandable medical implant 1 that is shown has been laterally expanded. Additionally, the fill material may generate some amount of additional longitudinal lengthening or expansion of the biasing member 20 and the expandable medical implant 1 overall. Fill material may also maintain one or both of longitudinal and lateral expansion and stabilize the first vertebra 1 relative to the second vertebra 2. In the illustrated embodiment, fill material is introduced into the expandable medical implant 1 through the port 26 in the extension 24. As shown in FIG. 6C, the port 26 passes through the first end 21 of the biasing member 20 and would communicate with a membrane placed over the biasing member 20 to fill the membrane. In other embodiments, fill material may be introduced at any effective location on the expandable medical implant 1, including but not limited to, directly into a membrane or into either or both of first and second ends of a biasing member or similar components. Fill material may be moved into the expandable medical implant 1 by pressure or force generated by a syringe, injector, multi-stage injector, central pressurization reservoir, or any effective system or device. The fill material may be fluid that is introduced only to expand the implant, or may be a final fill material. When the fluid introduced to expand the implant is not, or is not a component of, the final fill material, the fluid may be removed from the implant and be replaced in whole or in part by the fill material. The introduced fluid may also be a part of a multi-part fill material.

Another embodiment of the invention is a method of stabilizing a portion of a vertebral column. The embodiment may include removing at least a portion of one or more vertebrae from a space between a first vertebra and a second vertebra. As applied to the embodiment illustrated in FIGS. 7A-7C, an entire vertebra has been removed from between the first vertebra V1 and the second vertebra V2. In some embodiments, only a part of a vertebra may be removed and replaced by an implant, as for example, in the case of a hemi-vertebrectomy. As illustrated in this and other embodiments herein, the vertebra listed as the first vertebra is in a superior position and the vertebra listed as the second vertebra is in an inferior position. In other embodiments, the positioning of the first and second vertebra V1, V2, may be reversed.

The embodiment may also include inserting a medical implant having a length into the space between the first vertebra V1 and the second vertebra V2. As shown in FIGS. 7A-7C, the expandable medical implant 1 has a length between the longitudinal extents of the first end 21 and the second end 22 and is inserted into the space between the first vertebra V1 and the second vertebra V2. The expandable medical implant 1 is illustrated being forced against the second vertebra V2 to decrease the length of the expandable medical implant 1 in FIG. 7B. The force F is shown applied to the extension 24 to decrease the length in the illustrated embodiment. The force F is a pushing linear force as illustrated, but in other embodiments, the force may be a pulling, twisting, combination force, or any effective force to decrease the length of a complementary expandable medical implant. The expandable medical implant 1 may be allowed to expand in length to come into contact with the first vertebra V1. An expandable medical implant 1 with an expanded length is illustrated in FIG. 7C.

The embodiment may include introducing a fill material into the medical implant to expand the medical implant laterally to occupy a portion of the space between the first vertebra V1 and the second vertebra V2. As illustrated in FIG. 7C, the expandable medical implant 1 has had a fill material introduced into it such that it has been expanded laterally to occupy a portion of the space between the first vertebra V1 and the second vertebra V2. The fill material introduced may, for example and without limitation, be the fill material 100 described in more detail herein.

In some embodiments, a cavity 32 (FIG. 7A) is formed in the second vertebra V2 and a portion of the medical implant is inserted into the cavity 32. As shown in FIG. 7B, a second end 22 of the biasing element 20 has been inserted into the cavity 32. In some embodiments, a similar cavity may be formed in the endplate of an opposite vertebra, such as first vertebra V1 depicted in FIGS. 7A-7C. In this example, the first end 21 of the biasing element 20 may be inserted in the cavity formed in the endplate of the first vertebra V1 as the expandable medical implant 1 is allowed to expand.

The expandable medical implant is shown in FIGS. 7A-7C as being implanted from a generally posterior approach. However, embodiments of the invention may include implantation from any surgical approach, including but not limited to, posterior, lateral, anterior, transpedicular, lateral extracavitary, in conjunction with a laminectomy, in conjunction with a costotransversectomy, or by any combination of these and other approaches.

Various method embodiments of the invention are described herein with reference to particular expandable medical implants. However, in some circumstances, each disclosed method embodiment may be applicable to each of the expandable medical implants, or to some other implant operable as disclosed with regard to the various method embodiments.

Terms such as lower, upper, anterior, posterior, inferior, superior, lateral, medial, side, top, and the like have been used herein to note relative positions. However, such terms are not limited to specific coordinate orientations, but are used to describe relative positions referencing particular embodiments. Such terms are not generally limiting to the scope of the claims made herein.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. A method of stabilizing spaced apart skeletal structures comprising:
   providing an expandable medical implant comprising:
      a membrane defining a volume and including an upper surface, a substantially opposite lower surface, and a lateral diameter, and
      a biasing member including a first end, a substantially opposite second end, and a lateral diameter, wherein the biasing member is coupled to the membrane;
   grasping the first end of the biasing member;
   placing the second end of the biasing member against a second skeletal structure to compress the biasing member;
   aligning the first end of the biasing member with a first skeletal structure;
   releasing compression of the biasing member to allow the expandable medical implant to contact the first skeletal structure; and
   introducing fill material into the expandable medical implant to one or both maintain expansion and cause expansion of the expandable medical implant.

2. The method of claim 1 wherein the act of grasping the first end of the biasing member includes directly connecting to the first end of the biasing member with a tool.

3. The method of claim 1 wherein the act of grasping the first end of the biasing member includes connecting to an extension from the first end of the biasing member.

4. The method of claim 3 wherein the act of introducing fill material into the expandable medical implant includes introducing fill material through the extension.

5. The method of claim 1 wherein the act of placing the second end of the biasing member against a second skeletal structure includes placing the second end of the biasing member in a cavity in the second skeletal structure.

6. A method of stabilizing a portion of a vertebral column comprising:
   removing at least a portion of one or more vertebrae from a space between a first vertebra and a second vertebra;
   inserting a medical implant having a length into the space between the first vertebra and the second vertebra;
   forcing the medical implant against the second vertebra to decrease the length of the medical implant;
   allowing the medical implant to expand in length to come into contact with the first vertebra; and
   introducing a fill material into the medical implant to expand the medical implant laterally to occupy a portion of the space between the first vertebra and the second vertebra.

7. The method of claim 6 wherein the act of inserting the medical implant having a length into the space includes inserting the medical implant from a generally posterior approach to the vertebral column.

8. The method of claim 6, further comprising creating a cavity in the second vertebra into which a portion of the medical implant is inserted.

9. The method of claim 6, further comprising creating a cavity in the first vertebra into which a portion of the medical implant is allowed to expand.

* * * * *